United States Patent
Karavas et al.

(10) Patent No.: US 8,187,635 B2
(45) Date of Patent: May 29, 2012

(54) PHARMACEUTICAL COMPOSITION CONTAINING A PYRROLIDONE ANTICONVULSANT AGENT AND METHOD FOR THE PREPARATION THEREOF

(75) Inventors: Evangelos Karavas, Pallini Attikis (GR); Efthimios Koutris, Pallini Attikis (GR); Dimitrios Bikiaris, Salonika (GR); Vicky Samara, Pallini Attikis (GR); Ioanna Koutri, Pallini Attikis (GR); Eleni Stathaki, Pallini Attikis (GR)

(73) Assignee: Pharmathen S.A, Pallini, Attikis (GR)

( * ) Notice: Subject to any disclaimer, the term of this patent is extended or adjusted under 35 U.S.C. 154(b) by 113 days.

(21) Appl. No.: 12/739,475

(22) PCT Filed: Oct. 16, 2007

(86) PCT No.: PCT/EP2007/008952
§ 371 (c)(1), (2), (4) Date: Apr. 23, 2010

(87) PCT Pub. No.: WO2009/049642
PCT Pub. Date: Apr. 23, 2009

(65) Prior Publication Data
US 2011/0033538 A1    Feb. 10, 2011

(51) Int. Cl.
A61K 9/28 (2006.01)

(52) U.S. Cl. .................................................. 424/474
(58) Field of Classification Search .................. None
See application file for complete search history.

(56) References Cited

U.S. PATENT DOCUMENTS

| | | | |
|---|---|---|---|
| 2004/0259933 A1* | 12/2004 | Dolitzky et al. | 514/424 |
| 2006/0039968 A1* | 2/2006 | Manikandan et al. | 424/464 |
| 2006/0141037 A1 | 6/2006 | Mehta | |
| 2006/0204578 A1* | 9/2006 | Vergez et al. | 424/473 |
| 2007/0269511 A1* | 11/2007 | Bockbrader et al. | 424/468 |

FOREIGN PATENT DOCUMENTS

| | | |
|---|---|---|
| IL | EP1810676 A | 7/2007 |
| WO | WO2004069796 A | 8/2004 |
| WO | WO2006102750 A | 10/2006 |

* cited by examiner

*Primary Examiner* — Bethany Barham
(74) *Attorney, Agent, or Firm* — Aliki K. Collins; AKC Patents LLC

(57) ABSTRACT

The present invention relates to a pharmaceutical formulation of solid dosage forms comprising a therapeutically effective amount of a pyrrolidone anticonvulsant agent, and in particular Levetiracetam or a pharmaceutical acceptable salt or derivative thereof, in combination with an effective diluent, such as Dibasic Calcium Phosphate, and additional pharmaceutical excipients, and a process for the preparation thereof by wet granulation.

14 Claims, No Drawings

PHARMACEUTICAL COMPOSITION CONTAINING A PYRROLIDONE ANTICONVULSANT AGENT AND METHOD FOR THE PREPARATION THEREOF

TECHNICAL FIELD OF THE INVENTION

The present invention relates to improved pharmaceutical formulations for oral administration and in particular to a pharmaceutical formulation for oral administration comprising a therapeutically effective quantity of a pyrrolidone anticonvulsant agent, and more particularly Levetiracetam or a pharmaceutical acceptable salt or derivative thereof, in combination with an effective amount of Dibasic Calcium Phosphate and a method for the preparation thereof.

BACKGROUND OF THE INVENTION

Anticonvulsants, also called antiepileptics, belong to a diverse group of pharmaceuticals used in prevention of the occurrence of epileptic seizures. Epilepsy is a serious neurological disorder characterized by recurrent, unprovoked spontaneous seizures. These seizures are transient signs and/or symptoms, caused by abnormal, excessive or synchronous neuronal activity in the brain.

More and more, anticonvulsants are also find ways into the treatment of bipolar disorder, since many seem to act as mood stabilizers. The goal of an anticonvulsant is to suppress the rapid and excessive firing of neurons that start a seizure. An effective anticonvulsant would prevent the spread of the seizure within the brain and offer protection against possible excitotoxic effects that may result in brain damage. However, anticonvulsants themselves have been linked to lowered IQ and cell apoptosis. Many anticonvulsants block Sodium ($Na^+$) channels, Calcium ($Ca^{2+}$) channels, AMPA receptors or NMDA receptors. Some anticonvulsants inhibit the metabolism of GABA or increase its release.

Levetiracetam, the S-enantiomer of α-ethyl-2-oxo-1-pyrrolidine acetamide, constitutes an anticonvulsant medication of the pyrrolidine group and is used for the treatment of epilepsy. It has been approved as medication for adjunctive treatment of partial seizures, has no clinically significant drug interactions and has limited adverse effects. Moreover, it has fewer negative interactions with other antiepileptic drugs or anticonvulsants, and may be used in combination with other antiepileptic drugs in the treatment of epilepsy. Additionally, levetiracetam offers the advantages of 100% bioavailability, lack of protein binding and pure renal excretion.

Levetiracetam is a white to off-white crystalline powder with a faint odor and a bitter taste. It is very soluble in water, freely soluble in chloroform and in methanol, sparingly soluble in acetonitrile and practically insoluble in n-hexane.

Based upon the physicochemical properties of the active agent Levetiracetam, the major problem encountered when formulating Levetiracetam is the high solubility of the active ingredient, as well as the need of comprising a high amount of the active agent within the final tablet dosage form.

Various methods are already known for the industrial preparation of oral dosage forms comprising the pyrrolidone anticonvulsant agent levetiracetam or a pharmaceutical acceptable salt or derivative thereof, as an active ingredient due to its useful therapeutic properties. However, the prior art has encountered substantial difficulties in the production of the oral solid formulations of sufficient hardness and friability.

High soluble active ingredients in high dosage forms impose many problems in formulating them. Dry granulation methods are difficulty applicable in such case because it is not easy to achieve adequate hardness thus tablets become friable and exhibit poor binding characteristics. Wet granulation method applies better binding characteristics to the formulation but the granulation medium has to be chosen carefully, as well as the excipients used to achieve good hardness and friability. A dosage form with appropriate physical characteristics avoids future problems such as chipping or breaking during packaging and transport and during tumbling in the film coating pan.

If a tablet is too friable, it will chip or break during packaging and transport. According EP Pharmacopoeia, pharmaceutical tablets should have a friability not exceeding 1% with a Carr Index from 1-25. In several studies, it has been tried to increase the hardness and friability of levetiracetam tablets by increasing the compression force, decreasing the proportion of lubricant and increasing the proportion of binder, but found in each case that a sufficiently hard and non-friable tablet could not be produced in a practical way.

Furthermore, the disintegration performance of the levetiracetam tablet is also quite long and therefore any possible solution to the hardness and friability problem should not have a substantial deleterious effect on either the disintegration time or lubrication of the tablet. There is also a need to mask the bitter taste of levetiracetam.

WO 2007/012439 discloses a pharmaceutical composition which comprises levetiracetam and 2.0 to 9.0% per weight of disintegrant, 0.0 to 3.0% per weight of gliding agent, 0.5 to 6.0% per weight of binder, and 0.0 to 1.0% per weight of lubricant, with respect to the total weight of the pharmaceutical composition, as well as a process for the preparation thereof.

WO 2006/102750 discloses a process for the preparation of a solid oral pharmaceutical formulation of levetiracetam, comprising wet granulation of a pharmaceutical blend comprising the active agent and simultaneous fluid bed drying the blend. In fact, the preparation process is characterized by a combined granulation and fluid bed drying step.

Although each of the above patents represents an attempt to overcome the hardness and friability problems associated with pharmaceuticals compositions comprising a high dose and high soluble anticonvulsant agent such as levetiracetam, there still exists a need for improving the mechanical strength of such pharmaceutical compositions.

SUMMARY OF THE INVENTION

It is, therefore, an object of the present invention to provide an improved solid dosage formulation for oral administration containing a high portion of a pyrrolidone anticonvulsant agent, and in particular levetiracetam or a pharmaceutical acceptable salt or derivative thereof as an active ingredient, which overcomes the deficiencies of the prior art.

It is another object of the present invention is to provide a solid dosage formulation for oral administration containing a pyrrolidone anticonvulsant agent, and in particular levetiracetam or a pharmaceutical acceptable salt or derivative thereof as an active ingredient, which has a sufficient hardness and friability with satisfactory disintegration time, lubrication properties, flow properties and good pharmacotechnical properties.

Moreover, it is another object of the present invention to provide a solid dosage formulation for oral administration containing a pyrrolidone anticonvulsant at a high concentration, and in particular levetiracetam or a pharmaceutical acceptable salt or derivative thereof as an active ingredient, which can be prepared in dosage forms of different strength by proportionally adjusting the quantities of the excipients and the active ingredient, thereby providing excellent pharmacotechnical and physicochemical characteristics, regarding its storage and manufacturing procedure stability, without affecting the dissolution profile and bioavailability of the active ingredient.

A further aspect of the present invention is to provide a method for the preparation of a stable solid dosage formulation for oral administration containing a high portion of a pyrrolidone anticonvulsant agent, and in particular levetiracetam or a pharmaceutical acceptable salt or derivative thereof as an active ingredient, thereby improving the friability, hardness, flow properties and the pharmacotechnical characteristics of the composition.

In accordance with the above objects of the present invention, a pharmaceutical composition for oral administration is provided comprising a high proportion of a pyrrolidone anticonvulsant agent such as Levetiracetam or a pharmaceutical acceptable salt or derivative thereof as an active ingredient, and an effective quantity of Dibasic Calcium Phosphate to improve friability, hardness and flow properties of the composition.

According to another embodiment of the present invention, a process for the preparation of solid dosage forms for oral administration such as tablets, capsules and sachets, containing a pyrrolidone anticonvulsant agent such as Levetiracetam or a pharmaceutical acceptable salt or derivative thereof as an active ingredient and an effective amount of Dibasic Calcium Phosphate to improve friability, hardness and flow properties of the composition is provided, which comprises:

Forming a granulating solution by agitating purified water with the total quantity of a binder such as HPC;
Forming a homogenous mixture by mixing the total quantity of said active ingredient with the total quantity of Dibasic Calcium Phosphate, and optionally at least a diluent, such as MCC and a portion of the total quantity of a disintegrant, such as Cross Povidone;
Kneading the above mixture with the granulating solution;
Sieving the wetted mass through a sieve and forming granules
Drying the granules;
Sieving the dried granules through a sieve to achieve the desired granule size;
forming a second blend by mixing the remaining amount of the disintegrant and the total quantity of any other optional excipient such as a binder, lubricant, a colorant, and/or a glidant until uniform;
blending the above formed granules with the second blend, and
Formulating the resulting mixture in a solid dosage form either by compressing it into a desired tablet form or by filling capsules or sachets.

Further preferred embodiments of the present invention are defined in dependent claims 2 to 10 and 12 to 13.

Other objects and advantages of the present invention will become apparent to those skilled in the art in view of the following detailed description.

DETAILED DESCRIPTION OF THE INVENTION

For the purposes of the present invention, the term "pharmaceutically acceptable salt" refers to a salt that is not toxic at the specific therapeutic dosage and to a salt that does not independently possess significant pharmacological activity.

An excipient is considered to be "incompatible" with an active ingredient (a pyrrolidone anticonvulsant agent such as levetiracetam or a pharmaceutical acceptable salt or derivative thereof) if it inhibits the dissolution rate of said active ingredient, that is to say, if said active ingredient (a pyrrolidone anticonvulsant agent such as levetiracetam or a pharmaceutical acceptable salt or derivative thereof) dissolves less or slower in the presence of said excipient when compared with the dissolution rate of said active ingredient on its own. The terms "incompatibility", "compatible" and "compatibility" are defined accordingly.

The active ingredient (a pyrrolidone anticonvulsant agent such as levetiracetam or a pharmaceutical acceptable salt or derivative thereof) contained in a dosage form is "bioavailable", if when administered in a dosage form is released from the dosage form, absorbed and reaches, at least the same, concentration levels in plasma as any of the marketed products containing the same quantity of the same active ingredient and intended for the same use.

Although the pharmaceutical composition may be in various forms, the preferred solid forms are tablets, capsules and caplets.

The improved solid pharmaceutical composition of the present invention is characterized by physicochemical properties suitable for the tablet formulation by wet granulation, the adequate release rate of the active ingredient (a pyrrolidone anticonvulsant agent such as levetiracetam or a pharmaceutical acceptable salt or derivative thereof) and the storage stability, by employing suitable pharmaceutically acceptable excipients.

The pharmacotechnical properties of pharmaceutical tablets include friability, hardness and flowability of the granules. Some of the problems that are encountered when producing tablets comprising high dose, high solubility active ingredients are friction and shock that most often cause tablets to chip or break.

Generally, the mechanical strength of a tablet formulation provides a measure of the bonding potential of the tablet contents and this information depends upon the selection of suitable excipients.

Tablet friability is defined as the percentage value of weight loss due to abrasion. A maximum weight loss of not more than 1% of the weight of the tablets being tested during the friability test is considered generally acceptable.

The friability test is closely related to the tablet hardness and is designed to evaluate the ability of the tablet to withstand abrasion during packaging and handling.

Tablet hardness constitutes another important pharmacotechnical property during tablet manufacture. Tablet hardness is associated with several tablet properties, including density and porosity. Hardness generally increases with normal storage of tablets, and depends on the shape, chemical properties, binding agent, as well as pressure applied during compression. If a tablet is too hard, then it may not disintegrate in the required period of time to meet the dissolution specifications. In contrast, if a tablet is too soft, then it may not be able to withstand the handling during subsequent processing, such as coating or packaging.

Another significant important property determining the mechanical strength of tablets is the flow property or fluidity. Flow property or fluidity is a characteristic required in order to produce tablets of a consistent weight and uniform strength. This means that good flowability is desirable for content uniformity and less weight variation in final tablets. In addition to that, compressibility is required to form a stable, intact compact mass when pressure is applied. Pharmaceutical formulations with acceptable flow property and compressibility characteristics for granules can be obtained by incorporating suitable excipients. Flow property of tablet granules is defined via the known term "Carr's Compressibility Index".

Furthermore, another property of significant importance during the evaluation of tablets is tablet dissolution. The dissolution rate of the drug from the primary particles of the tablet constitutes the important factor in drug absorption and for many formulations is the rate-limiting step. Therefore, the dissolution rate is an indication of the availability of the active ingredient from the tablet.

As already mentioned certain pyrrolidone anticonvulsant agents have high solubility and their tendency gets stronger when they are formulated and mixed with excipients or other active substances.

It has been surprisingly found that the object of the present invention is achieved by employing Dibasic Calcium Phosphate, as an effective diluent in order to improve friability, hardness and flow properties of the composition.

Dibasic calcium phosphate constitutes a diluent with excellent flowability and compressibility properties resolving that way flow and hardness problems associated with high dose and high solubility active ingredient formulations. It is practically insoluble in ethanol, ether, and water, and soluble in dilute acids. It is widely used in tablet formulations because of its compaction properties, and the good flow properties. It is also non hygroscopic and stable at room temperature.

Dibasic calcium phosphate is a white, odorless, tasteless crystalline powder. It is not consisted of individual crystals but aggregates of crystallites that undergo fragmentation caused by brittle fracture upon compaction and thus promoting inter-particulate interaction by creating numerous clean surfaces for bonding.

Moreover, any excipient may optionally be added to the above composition, provided that they are compatible with the active ingredient of the composition, in order to overcome problems associated with the poor flow properties and unfavorable pharmacotechnical characteristics of these substances, and in order to increase the stability and the dissolution rate of the finished dosage form, and provide a product exhibiting excellent bioavailability.

Furthermore, Microcrystalline Cellulose is also used in the tablet of the present invention as a diluent, because of its unique compressibility and carrying capacity. It compacts well under minimum compression pressures. Further, it has high binding capability, and creates tablets that are hard, stable, yet disintegrate rapidly.

Another excipient used in the tablet of the present invention is Crospovidone, as tablet disintegrant. In more detail, the capillary activity of Crospovidone for water is responsible for its tablet disintegration property. Cross linked polyvinyl pyrrolidone possesses maximum moisture absorption and hydration capacity. It also possesses apparent binding property resulting in low percent of tablet friability, where it is employed as disintegrant even in low concentration within the range of 0.5 and 5 percent.

Another pharmaceutical ingredient used in the tablet formulation of the present invention is Hydroxypropyl cellulose as a binder, in order to improve tablet hardness. This improvement in tablet hardness is proved from the pharmacotechnical tests performed.

The present invention can be applied in the formulation of tablets, capsules, caplets, sachets or other solid dosage forms for oral administration of an active ingredient having friability, hardness and flow properties problems.

Furthermore, it is possible to prepare dosage forms of different strength using appropriate quantity of the same composition, thereby limiting the cost of production and minimizing the number, and consequently the cost, of clinical studies required for the approval of the product by the authorities.

Therefore, in a first embodiment, the present invention provides a pharmaceutical composition comprising from about 40% to 90% by weight of Levetiracetam or salt thereof and from about 0.5% to 20% by weight of Dibasic Calcium Phosphate. The weight ratio of Levetiracetam or salt thereof to Dibasic Calcium Phosphate is preferably 2:1 to 180:1.

More preferred pharmaceutical compositions according to the present invention comprise approximately 0.5% to 20%, more preferably 0.75% to 15% and most preferably 1% to 15% by weight of Dibasic Calcium Phosphate.

The preferred pharmaceutical compositions are in the form of solid dosage forms for oral administration such as tablets, capsules, caplets, troches, pastilles, pills, lozenges and the like, in all shapes and sizes, coated or uncoated.

All percentages stated herein are weight percentages based on total composition weight, unless otherwise stated.

Another embodiment of the present invention is the use of the wet granulation process for the preparation of solid dosage forms for oral administration such as tablets, capsules and sachets containing a pyrrolidone anticonvulsant agent such as levetiracetam or a pharmaceutical acceptable salt or derivative thereof as an active ingredient, which comprises:

Forming a granulating solution by dissolving the total quantity of a binder, such as HPC into purified water;

Forming a first homogenous blend by mixing the total quantity of said active ingredient with the total quantity of Dibasic Calcium Phosphate to improve friability, hardness and flow properties of the composition, and optionally at least the total quantity of a diluent, such as MCC and a portion of the total quantity of a disintegrant, such as Cross Povidone;

Kneading the above mixture with the granulating solution;

Sieving the wetted mass through a sieve and forming granules

Drying the granules;

Sieving the dried granules through a sieve to achieve the desired granule size;

forming a second blend by mixing the remaining quantity of the disintegrant, such as Cross Povidone and the total quantity of at least one optional excipient such as binder, surfactant, disintegrant, lubricant, colorant, and/or glidant until uniform, blending the above formed granules with the second blend, and Formulating the resulting mixture in a solid dosage form either by compressing it into a desired tablet form or by filling capsules or sachets.

The tablets are optionally coated by water soluble coating agents.

Although the pharmaceutical composition may be in various forms, the preferred solid forms are tablets, capsules and caplets.

According to the desired properties of the composition, any number of ingredients may be selected, alone or in combination, based upon their known uses in preparation of solid dosage form composition.

Such ingredients include, but are not limited to, diluents, binders, compression aids, disintegrants, surfactants, wetting agents, glidants, lubricants, flavours, water scavengers, colorants, sweetener, coating agents and preservatives.

The optional excipients must be compatible with the selective estrogen receptor modulator or the salt thereof so that it does not interfere with it in the composition.

Diluents may be, for example, calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose maltodextrin, maltitol. Binders may be, for example, acacia mucilage, alginic acid, carbomer, carboxymethylcellulose calcium, carboxymethylcellulose sodium, microcrystalline cellulose, powdered cellulose, ethyl cellulose, gelatin, liquid glucose, guar gum, hydroxyethyl cellulose, hydroxypropyl cellulose, hydroxypropylmethyl cellulose, maltodextrin, methylcellulose, polydextrose, polyethylene oxide, povidone, sodium alginate, starch paste, pregelatinized starch, sucrose.

Disintegrants may be, for example, alginic acid, carbon dioxide, carboxymethylcellulose calcium, carboxymethylcellulose sodium, microcrystalline cellulose, powdered cellulose, croscarmellose sodium, crospovidone, sodium docusate, guar gum, hydroxypropyl cellulose, methylcellulose, polacrilin potassium, poloxamer, povidone, sodium alginate, sodium glycine carbonate, sodium lauryl sulfate, starch, pregelatinized starch.

Surfactants may be, for example, poloxamer, pluronic, ethoxylated castor oil, polyglycolyzed glycerides, acetylated monoglycerides, sorbitan fatty acid esters, polyoxyethylene sorbitan fatty acid esters, monoglycerides or ethoxylated derivatives thereof, diglycerides or polyoxyethylene derivatives thereof, as well as sodium docusate or sodium lauryl sulphate.

Glidants may be, for example, calcium silicate, powdered cellulose, starch, talc, colloidal silicon dioxide.

Lubricants may be e.g. magnesium stearate, polyethylene glycol 4000, polyethylene glycol 6000, sodium lauryl sulfate, starch, talc.

The following examples illustrate preferred embodiments in accordance with the present invention without limiting the scope or spirit of the invention:

EXAMPLES

As already mentioned the selection of the excipients is critical in order to fulfill the objects of the present invention. First of all the preferred excipients should provide to the granule good compressibility and flowability. Then those excipients should be compatible with the active ingredient.

Levetiracetam was tested for its compatibility with several pharmaceutically acceptable excipients comprising the above mentioned properties. The impurity profile of the active ingredient with sodium starch glycolate (Primojel) and PVP was not acceptable.

The following examples represent attempts on the bases of the current invention using excipients that are compatible with Levetiracetam.

Example 1

Tablet of Levetiracetam Composition 1

| Ingredients | % |
| --- | --- |
| Internal phase | |
| Levetiracetam | 74.63 |
| Starch 1500 | 3.50 |
| MCC | 3.37 |
| Cross Povidone | 2.00 |
| HPC | 8.00 |
| External phase | |
| Cross Povidone | 2.00 |
| Starch 1500 | 3.50 |
| Aerosil | 2.00 |
| Magnesium Stearate | 1.00 |
| Total | 100 |

Tablets of the above formulation were prepared according to the following manufacturing process: Levetiracetam, a portion of the total quantity of Starch 1500, the total quantity of MCC as filler and a portion of the total quantity of Cross Povidone as a disintegrant were admixed to complete homogeneity. The total quantity of HPC as a binder was dissolved in a mixture of ethanol and water (1:1) and stirred for an adequate period of time till it was completely dissolved. The first blend was kneaded with the granulating solution described above until it becomes homogenous. Sieving the resulting mixture through a sieve and forming the granules. Drying the granules and sieving. Subsequently, the remaining quantity of Cross Povidone, the remaining quantity of Starch 1500, the total amount of Aerosil and the total amount of Mg stearate were added in the above formed granules and mixed.

Finally, it was formulated in a solid dosage form either by compressing it into a desired tablet form. Subsequently, the tablets were film-coated.

The produced tablets were tested for content uniformity, disintegration, water content and dissolution proving that they are meeting the specifications.

The tablets of example 1 had low hardness (<70 Nt).

Example 2

Tablet of Levetiracetam Composition 2

| Ingredients | % |
| --- | --- |
| Internal phase | |
| Levetiracetam | 74.63 |
| Dicalcium Phosphate | 6.00 |
| MCC | 5.20 |
| Cross Povidone | 4.00 |
| HPC | 6.00 |
| External phase | |
| Cross Povidone | 3.17 |
| Magnesium Stearate | 1.00 |
| Total | 100 |

Tablets of the above formulation were prepared according to the following manufacturing process: Levetiracetam, the total quantity of Dibasic Calcium Phosphate, the total quantity of MCC as filler and a portion of the total quantity of Cross Povidone as a disintegrant were admixed to complete homogeneity. The total quantity of HPC as a binder was dissolved in a mixture of ethanol and water (1:1) and stirred for an adequate period of time till it was completely dissolved. The first blend was kneaded with the granulating solution described above until it becomes homogenous. Sieving the resulting mixture through a sieve and forming the granules. Drying the granules and sieving. Subsequently, the remaining quantity of Cross Povidone and the total amount of Mg stearate were added in the above formed granules and mixed.

Finally, it was formulated in a solid dosage form by compressing it into a desired tablet form. Subsequently, the tablets were film-coated, by water soluble coating agents.

The tablets of example 2 had good flow properties; however the hardness (<70 Nt) of the tablets was not satisfactory.

Changing the granulation medium from a mixture of EtOH: $H_2O$ 1:1 to water 100%, in order to take advantage of water's binding properties, resulted in an improvement to the tablets hardness (>65 Nt). The release rate from the tablets of example 2 was less than 80% in 15 minutes, so not satisfactory for an immediate release composition.

Example 3

Tablet of Levetiracetam Composition 3

| Ingredients | % |
|---|---|
| Internal phase | |
| Levetiracetam | 74.63 |
| Dicalcium Phosphate | 7.00 |
| MCC | 5.20 |
| Cross Povidone | 4.00 |
| HPC | 6.00 |
| External phase | |
| Cross Povidone | 3.17 |
| Total | 100 |

Tablets of the above formulation were prepared according to the following manufacturing process: Levetiracetam, the total quantity of Dibasic Calcium Phosphate, the total quantity of MCC as filler and a portion of the total quantity of Cross Povidone as a disintegrant were admixed to complete homogeneity. The total quantity of HPC as a binder was dissolved in water and stirred for an adequate period of time till it was completely dissolved. The first blend was kneaded with the granulating solution described above until it becomes homogenous. Sieving the resulting mixture through a sieve and forming the granules. Drying the granules and sieving. Subsequently, the remaining quantity of Cross Povidone was added in the above formed granules and mixed. Finally, it was formulated in a solid dosage form either by compressing it into a desired tablet form. Subsequently, the tablets were film-coated.

The tablets manufactured according to example 3 showed extremely improved hardness (>128 Nt) and dissolution rate (93% in 15 min).

Example 4

Tablet of Levetiracetam Composition 4

| Ingredients | % |
|---|---|
| Internal phase | |
| Levetiracetam | 74.63 |
| Dicalcium Phosphate | 7.00 |
| MCC | 8.20 |
| Cross Povidone | 4.00 |
| HPC | 3.00 |
| External phase | |
| Cross Povidone | 3.17 |
| Total | 100 |

Tablets of the composition 4 of Example 4 were prepared according to the manufacturing process used in Example 3.

Even though the mechanical properties and dissolution rate of the composition 3 were acceptable, the percentage of HPC in the composition was decreased, in order to enhance even more the dissolution rate.

One of the most critical pharmacotechnical tests is the dissolution test as it is strongly correlated with the bioavailability of the product. For the dissolution method a Paddles Apparatus II was run at 75 rpm, 37° C.±0.5° C., for 30 min, while as dissolution medium 500 ml of HCl 0.01N was used.

Dissolution rate results for composition 4 tested are given in Table 1. The results show that composition 4 is completely dissolved in about 30 minutes.

TABLE 1

Physicochemical characteristics of Levetiracetam 1,000 mg composition of example 4

| Test parameters | Levetiracetam 1,000 mg composition of example 4 | |
|---|---|---|
| Hardness | 152 Nt | |
| Disintegration Time | 7'25"-10'20" | |
| Dissolution | Time (min) | % Released |
| | 5 | 68.76 |
| | 10 | 88.76 |
| | 15 | 98.01 |
| | 20 | 100.22 |
| | 25 | 99.75 |
| | 30 | 99.94 |

Another objects of the present invention was to prepare a pharmaceutical composition that is stable, said active ingredient does not degradates and remains stable for a long period of storage time. For this reason, composition 4 was packed in PVC/PE/PVDC Aluminum blisters and exposed to normal (25° C.±2° C./60%±5% RH) stability studies according to the current ICH guidelines. The stability results after 12 months are shown in the table 2 below.

The composition 4 described above was investigated for its scalability, while a process validation was performed in order to prove the repeatability and accuracy of the manufacturing process and the proposed formulation.

The validation process showed that the composition and the manufacturing process are suitable in order to provide a repeatable and high quality product.

TABLE 2

Stability results for Levetiracetam 1,000 mg film-coated tablets (composition 4) at 25° C./60% RH

| Control Tests | Limits | Time (months) | | | | |
|---|---|---|---|---|---|---|
| | | 0 | 3 | 6 | 9 | 12 |
| Hardness | NLT 60N | 168N | 159N | 154N | 152N | 158N |
| Loss on Drying | NMT 4.0% | 2.1% | 2.4% | 2.4% | 2.3% | 2.2% |
| Disintegration | Max 30 min in water at 37° C. ± 1° C. | 3'10"-5'45" | 2'49"-5'11' | 3'15"-4'58" | 2'59"-5'20" | 3'13"-4'40" |
| Dissolution | Apparatus paddles, 50 rpm each tablet >80% in 30 min | 104.4% | 100.1% | 99.5% | 98.9% | 99.9% |
| Related Substances | (S)-2-Aminobutyramide Hydrochloride (LT1): NMT 0.10% | ND | ND | ND | ND | ND |
| | Any single impurity: NMT 0.10% | RRT 0.44: 0.01% | RRT 0.46: 0.01% | RRT 0.45: 0.01% | RRT 0.78: 0.02% | RRT 0.72: 0.01% |
| | | RRT 0.73: 0.03% | RRT 0.77: 0.03% | RRT 0.76: 0.02% | RRT 1.12: 0.01% | RRT 0.92: 0.01% |
| | | RRT 1.14: 0.02% | | | | RRT 1.14: 0.01% |
| | | RRT 1.25: 0.02% | RRT 1.13: 0.01% | RRT 1.13: 0.01% | RRT 1.22: 0.02% | RRT 1.24: 0.02% |
| | | RRT 1.28: 0.02% | RRT 1.23: 0.03% | RRT 1.23: 0.01% | RRT 1.25: 0.02% | RRT 1.27: 0.02% |
| | | RRT 1.40: 0.03% | RRT 1.26: 0.02% | RRT 1.26: 0.02% | RRT 1.37: 0.02% | RRT 1.39: 0.02% |
| | Total: NMT 0.50% | 0.13% | 0.10% | 0.07% | 0.09% | 0.09% |

The results show a good stability of the product and compatibility between the drug substance and the excipients proposed by the present invention. The excellent results regarding the physicochemical characteristics (such as good granule flowability and tablets with excellent hardness and friability), the excellent stability of the product as well as the simple and economic manufacturing process indicate the advantages of the present invention relative to the commonly used methods and excipients for the formulation of Levetiracetam.

While the present invention has been described with respect to the particular embodiments, it will be apparent to those skilled in the art that various changes and modifications may be made in the invention without departing from the spirit and scope thereof, as defined in the appended claims.

The invention claimed is:

1. A pharmaceutical composition for oral administration comprising a pyrrolidone anticonvulsant agent or a pharmaceutical acceptable salt or derivative thereof, as an active ingredient, and an effective quantity of a diluent agent configured to improve friability, hardness and flow properties of the composition, wherein said pyrrolidone anticonvulsant agent comprises Levetiracetam and wherein said diluent agent comprises Dibasic Calcium Phosphate and wherein said pharmaceutical composition comprises an immediate release composition, is free of magnesium stearate and has a hardness of >70 N in a tablet form.

2. The pharmaceutical composition according to claim 1, comprising 50% to 85% by weight of said Levetiracetam.

3. The pharmaceutical composition according to claim 1, wherein it comprises from about 40 to 90% by weight of said Levetiracetam or salt thereof, and from about 0.5 to 20% by weight of said Dibasic Calcium Phosphate.

4. The pharmaceutical composition according to claim 1, wherein the weight ratio of said Levetiracetam or salt thereof, to Dibasic Calcium Phosphate is preferably 2:1 to 180:1.

5. The pharmaceutical composition according to claim 1, comprising 45% to 85% by weight of said Levetiracetam or salt thereof.

6. The pharmaceutical composition according to claim 1, comprising 0.75% to 15% by weight of Dibasic Calcium Phosphate.

7. The pharmaceutical composition according to claim 1, comprising 1% to 15% by weight of Dibasic Calcium Phosphate.

8. The pharmaceutical composition according to claim 1, wherein it further comprises at least one optional excipient selected from the group consisting of diluents, binders, disintegrants, lubricants, and glidants.

9. The pharmaceutical composition according to claim 1, wherein it further comprises MCC, Crospovidone and HPC.

10. The pharmaceutical composition according to claim 1, comprising 0.5% to 20% by weight of Dibasic Calcium Phosphate.

11. A process for the preparation of a pharmaceutical composition for oral administration comprising
   forming a granulating solution by agitating purified water with the total quantity of a binder, wherein said binder comprises HPC;
   forming a homogenous mixture by mixing the total quantity of an active ingredient comprising a pyrrolidone anticonvulsant agent with the total quantity of an effective quantity of Dibasic Calcium Phosphate as an agent configured to improve friability, hardness and flow properties of the composition, and optionally at least a diluent, and a portion of the total quantity of a disintegrant, wherein said pyrrolidone anticonvulsant agent comprises Levetiracetam or a pharmaceutical acceptable salt or derivative thereof, said diluent comprises MCC and said disintegrant comprises Cross Povidone;

kneading the homogeneous mixture with the granulating solution;

sieving the wetted mass through a sieve and forming granules drying the granules;

sieving the dried granules through a sieve to achieve the desired granule size;

forming a second blend by mixing the remaining amount of the disintegrant, and the total quantity of any other optional excipient comprising one of a binder, lubricant, a colorant, and/or a glidant until uniform, blending the above formed granules with the second blend, and formulating the resulting mixture in a solid dosage form either by compressing it into a desired tablet form or by filling capsules or sachets; and wherein said pharmaceutical composition comprises an immediate release composition, is free of magnesium stearate and has a hardness of >70 N.

12. The pharmaceutical composition according to claim 1 comprising 40% to 90% by weight of Levetiracetam or salt thereof.

13. The process according to claim 11, wherein said tablet is coated with a water soluble coating agent.

14. A pharmaceutical composition for oral administration comprising: a pyrrolidone anticonvulsant agent or a pharmaceutical acceptable salt or derivative thereof, as an active ingredient; an effective quantity of a diluent agent configured to improve friability, hardness and flow properties of the composition; wherein said pyrrolidone anticonvulsant agent comprises Levetiracetam and wherein said diluent comprises Dibasic Calcium Phosphate and wherein said pharmaceutical composition comprises from about 40% to 90% by weight of said Levetiracetam, and from about 0.5% to 20% by weight of said Dibasic Calcium Phosphate; and wherein said pharmaceutical composition comprises an immediate release composition, is free of magnesium stearate and has a hardness of >70 N in a tablet form.

* * * * *